US011206982B2

United States Patent
Wang (10) Patent No.: US 11,206,982 B2
(45) Date of Patent: Dec. 28, 2021

(54) APPARATUS AND METHOD FOR FLUORESCENCE MOLECULAR TOMOGRAPHY

(71) Applicant: BOE TECHNOLOGY GROUP CO., LTD., Beijing (CN)

(72) Inventor: Guohe Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 355 days.

(21) Appl. No.: 15/983,163

(22) Filed: May 18, 2018

(65) Prior Publication Data
US 2019/0029518 A1 Jan. 31, 2019

(30) Foreign Application Priority Data

Jul. 25, 2017 (CN) .......................... 201710612381.2

(51) Int. Cl.
*A61B 5/00* (2006.01)
*G01N 21/64* (2006.01)
*G01N 21/47* (2006.01)

(52) U.S. Cl.
CPC .......... *A61B 5/0035* (2013.01); *A61B 5/0071* (2013.01); *A61B 5/0073* (2013.01);
(Continued)

(58) Field of Classification Search
CPC .......... G01N 21/6456; G01N 21/4795; G01N 21/6428; G01N 2201/103; A61B 5/0035;
(Continued)

(56) References Cited

U.S. PATENT DOCUMENTS

| 6,615,063 B1* | 9/2003 | Ntziachristos ....... A61B 5/0073 |
| | | 600/312 |
| 2003/0136901 A1* | 7/2003 | Ohtomo ................ G01S 1/7038 |
| | | 250/234 |

(Continued)

FOREIGN PATENT DOCUMENTS

| CN | 1994229 A | 7/2007 |
| CN | 101019018 A | 8/2007 |

(Continued)

OTHER PUBLICATIONS

First Office Action for Chinese Patent Application No. 201710612381.2 dated Aug. 28, 2019.

*Primary Examiner* — Christopher Koharski
*Assistant Examiner* — Kaitlyn E Selmer
(74) *Attorney, Agent, or Firm* — Calfee, Halter & Griswold LLP (57) ABSTRACT

An apparatus for fluorescence molecular tomography includes an exciting light source, a carrying stage, and a receiving apparatus. The carrying stage configured to carry an subject to be examined which receives the exciting light to excite fluorescence; the receiving apparatus comprising a fluorescence detector, an exciting light detector and a beam splitter, the beam splitter is configured to allow the fluorescence to exit in a first direction and the exciting light having passed through the subject to be examined to exit in a second direction, the fluorescence detector is positioned in the first direction to the beam splitter and configured to receive and transform the fluorescence into a first electrical signal. The exciting light detector is positioned in the second direction to the beam splitter and configured to receive and transform the exciting light having passed through the subject to be examined into a second electrical signal.

6 Claims, 5 Drawing Sheets

(52) U.S. Cl.
CPC ..... *G01N 21/4795* (2013.01); *G01N 21/6428* (2013.01); *G01N 21/6456* (2013.01); *A61B 2503/40* (2013.01); *G01N 2201/103* (2013.01)

(58) Field of Classification Search
CPC .. A61B 5/0073; A61B 5/0071; A61B 2503/40
See application file for complete search history.

(56) References Cited

U.S. PATENT DOCUMENTS

| | | | |
|---|---|---|---|
| 2005/0046836 A1* | 3/2005 | Olschewski | G01N 21/6458 356/318 |
| 2007/0231883 A1* | 10/2007 | Lindstrom | G01N 21/645 435/287.2 |
| 2009/0240138 A1 | 9/2009 | Yi | |
| 2012/0310083 A1* | 12/2012 | Friedman | A61F 9/008 600/431 |
| 2013/0137165 A1* | 5/2013 | Jung | G01N 21/6452 435/287.2 |
| 2015/0057549 A1* | 2/2015 | Flusberg | A61B 5/4064 600/476 |
| 2017/0105618 A1* | 4/2017 | Schmoll | G01B 9/02097 |
| 2017/0176338 A1* | 6/2017 | Wu | G01J 3/2823 |
| 2017/0339378 A1* | 11/2017 | Okumura | G06F 3/017 |

FOREIGN PATENT DOCUMENTS

| | | | |
|---|---|---|---|
| CN | 101365377 | A | 2/2009 |
| CN | 102741707 | A | 10/2012 |
| CN | 102830095 | A | 12/2012 |
| CN | 104267488 | A | 1/2015 |
| CN | 104597590 | A | 5/2015 |
| CN | 104597590 | A * | 5/2015 |
| CN | 104614353 | A | 5/2015 |
| CN | 104873212 | A | 9/2015 |
| CN | 106419837 | A | 2/2017 |
| CN | 106419837 | A * | 2/2017 |
| CN | 106562770 | A | 4/2017 |
| EP | 2698100 | A1 | 2/2014 |
| EP | 2859326 | A1 | 4/2015 |

* cited by examiner

APPARATUS AND METHOD FOR FLUORESCENCE MOLECULAR TOMOGRAPHY

CROSS REFERENCE

The present application claims the priority of Chinese Patent Application No. 201710612381.2, filed on Jul. 25, 2017, and the entire contents thereof are incorporated herein by reference as part of the present application.

TECHNICAL FIELD

The present disclosure relates to an apparatus for fluorescence molecular tomography and a method for fluorescence molecular tomography.

BACKGROUND

For many illnesses of mankind small animal pathological models may be built. Research of small animals may help know the pathogenesis of the illnesses, develop new medicines and evaluate efficacy of the medicines, and so on. Meanwhile, small animal molecular imaging techniques play an important role in the small animal research. The fluorescence molecular tomography (FMT) is a newly-developing small animal molecular imaging technique which may image the 3D spatial distribution of fluorescent substance in the body of a small animal, as compared with the conventional 2D fluorescence imaging, by collecting fluorescence emitting from the body surface of the small animal and information of exciting light, and building a model of light propagating through biological tissues. Moreover, FMT has advantages of such as noninvasiveness, high sensitivity, good specificity, safety and nonradiativeness and thus is paid wide attention to in the small animal research.

It should be noted that the information disclosed in the above BACKGROUND section is only to enhance understanding of the background of the disclosure, and thus may contain information which is not part of the prior art known to those skilled in the art.

SUMMARY

In one aspect of the disclosure, there is provided an apparatus for FMT coupled with a computer product and including:

an exciting light source configured to provide an exciting light;

a carrying stage configured to carry a subject to be examined which receives the exciting light to excite fluorescence;

a receiving apparatus comprising a fluorescence detector, an exciting light detector and a beam splitter, wherein the beam splitter is configured to allow the fluorescence to exit in a first direction and the exciting light having passed through the subject to be examined to exit in a second direction, the fluorescence detector is positioned in the first direction to the beam splitter and configured to receive and transform the fluorescence into a first electrical signal, and the exciting light detector is positioned in the second direction to the beam splitter and configured to receive and transform the exciting light having passed through the subject to be examined into a second electrical signal; and the computer product includes a processor configured to reconstruct a fluorescence distribution image based on the first and second electrical signals.

In some embodiments, the exciting light source, the receiving apparatus are rotatable relatively to the subject to be examined to enable the processor to generate a 3D fluorescence distribution image.

In some embodiments, the exciting light source and the receiving apparatus are fixedly positioned, while the carrying stage is rotatable to rotate the subject to be examined.

In some embodiments, the carrying stage is fixedly positioned, while the exciting light source and the receiving apparatus are rotatable about the carrying stage as a center.

In some embodiments, the exciting light source includes:
a laser configured to emit the exciting light; and
an exciting light adjusting mechanism configured to split the exciting light exiting from the laser into a plurality of exciting light beams.

In some embodiments, the exciting light adjusting mechanism comprises:
a splitting mirror having an optical axis at a selected angle with respect to the exciting light and configured to split the exciting light into two exciting light beams by reflection and transmission; and
a reflective mirror arranged parallel to the splitting mirror and configured to reflect and allow one of the exciting light beams having passed through the splitting mirror to be parallel to another exciting light beam.

In some embodiments, the exciting light adjusting mechanism includes:
a first splitting mirror having an optical axis at a selected angle with respect to the exciting light and configured to split the exciting light into two exciting light beams by reflection and transmission;
a second splitting mirror arranged parallel to the first splitting mirror and configured to split one of the exciting light beams having passed through the first splitting mirror into two exciting light beams;
a first reflective mirror arranged parallel to the first splitting mirror and configured to reflect and allow one of the exciting light beams having passed through the second splitting mirror to be parallel to another exciting light beam having passed through the second splitting mirror and another exciting light beam having passed through the first splitting mirror;
a third splitting mirror arranged perpendicular or parallel to the first splitting mirror and configured to split the another exciting light beam having passed through the first splitting mirror into two exciting light beams; and
a second reflective mirror arranged parallel to the third splitting mirror and configured to reflect and allow one of the exciting light beams having passed through the third splitting mirror to be parallel to another exciting light beam having passed through the third splitting mirror and the another exciting light beam having passed through the second splitting mirror.

In some embodiments, the exciting light adjusting mechanism includes:
a first splitting mirror having an optical axis at a selected angle with respect to the exciting light and configured to split the exciting light into two exciting light beams;
a second splitting mirror arranged parallel to the first splitting mirror and configured to split one of the exciting light beams having passed through the first splitting mirror into two exciting light beams;
a third splitting mirror arranged parallel to the second splitting mirror and configured to split one of the exciting light beams having passed through the second splitting mirror into two exciting light beams;

a first reflective mirror arranged parallel to the third splitting mirror and configured to reflect and allow one of the exciting light beams having passed through the third splitting mirror to be parallel to another exciting light beam; and the first, second and third splitting mirrors and the first reflective mirror are coaxially arranged in a direction either parallel or perpendicular to the exciting light to split the exciting light into four exciting light beams.

In some embodiments, the fluorescence detector includes:

an exciting light filer configured to filter out the exciting light; and a first imaging device configured to receive and transform the fluorescence into an electric signal.

In some embodiments, the exciting light detector includes:

a fluorescence filer configured to filter out the fluorescence; and a second imaging device configured to receive and transform the exciting light having passed through the subject to be examined into an electric signal.

In one aspect of the disclosure, there is provided a computer product coupled with the apparatus for fluorescence molecular tomography, which includes a processor configured to reconstruct a fluorescence distribution image based on the first and second electrical signals.

In some embodiments, the reconstruction of the fluorescence distribution image includes generation of a 3D fluorescence distribution image.

In some embodiments, the processor is configured to generate the 3D fluorescence distribution image within the subject to be examined based on the first and second electric signals, which includes:

obtaining from $$\frac{y_f}{y_x} = A\mu_f(r)$$

a 3D absorption coefficient distribution of fluorescence within the subject to be examined, where A is a projection matrix, $\mu_f(r)$ is 3D absorption coefficient distribution of fluorescence within the subject to be examined, $y_x$ is the intensity of the exciting light having passed through the subject to be examined and received by the exciting light detector, and $y_f$ is the intensity of the fluorescence received by the fluorescence detector.

In one aspect of the disclosure, there is provided a method for FMT applied in any of the aforesaid apparatus for FMT, the method for FMT comprising:

providing an exciting light;

controlling the carrying stage or the exciting light source and the receiving apparatus to rotate and stay according to a selected rule;

receiving and transforming the fluorescence into a first electric signal, and at the same time receiving and transforming the exciting light having passed through the subject to be examined into a second electric signal; and generating a fluorescence distribution image within a body of the subject to be examined based on the first and second electric signals.

In some embodiments, the step of generating the fluorescence distribution image within the body of the subject to be examined based on the first and second electric signals includes generating a 3D fluorescence distribution image within the subject to be examined based on the first and second electric signals.

In some embodiments, generating a 3D fluorescence distribution image within the body of the subject to be examined based on the first and second electric signals includes:

obtaining from $$\frac{y_f}{y_x} = A\mu_f(r)$$

a 3D absorption coefficient distribution of fluorescence within the body of the subject to be examined, where A is a projection matrix, $\mu_f(r)$ is 3D absorption coefficient distribution of fluorescence within the body of the subject to be examined, $y_x$ is the intensity of the exciting light having passed through the subject to be examined and received by the exciting light detector, and $y_f$ is the intensity of the fluorescence received by the fluorescence detector.

BRIEF DESCRIPTION OF THE DRAWINGS

The aforesaid and other features and advantages of the disclosure will become more apparent by describing in detail the exemplary embodiments of the disclosure with reference to the accompanying drawings.

DETAILED DESCRIPTION

Now a fuller description will be made to the exemplary embodiments in conjunction with the accompanying drawings. However, the exemplary embodiments may be implemented in various ways and should not be interpreted to be limited to those described here; instead, the embodiments are provided to enable the disclosure full and complete and fully convey the spirits thereof to those skilled in the art. The same numeral references through the drawings indicate the same or similar structures of which the detailed descriptions will be omitted.

According to relevant technique, a FMT apparatus usually uses a beam of laser as an exciting light. That method has a problem mainly in weak fluorescence excited by the exciting light, for a possible reason that the concentrated fluorescent substance is relatively far away from the incident position of the exciting light, or that the exciting light cannot excite all of the fluorescent substance for the fluorescent substance is distributed across many sites in the small animal body. As known by the inventor, it is possible to move the position of the exciting light to make a multiple-round scan so as to implement strong excitement of all fluorescent substance. The multiple-round scan, however, will certainly increase experimental time, which may cause discomfort for the small animal under experiment, then may cause the position of the small animal to change, and finally may cause inaccuracy of the experimental results. Furthermore, fluorescence reconstruction requires collecting an exciting light image and a fluorescence image at the same one position, while with the conventional method, a round of exciting light images is collected followed by collecting a round of fluorescence image. For the same reason, separation collections of exciting light images and fluorescence images no doubt cause increase of experimental time which may cause discomfort for the small animal under experiment, then may cause the position of the small animal to change, may result in that the fluorescence images and the exciting light images are not collected at the same positions, and may finally cause inaccuracy of the experimental results. Moreover, photobleaching may occur for the fluorescent substance over time. Accordingly, the longer the experimental time is, the more inaccurate the experimental results are.

Figure 1:
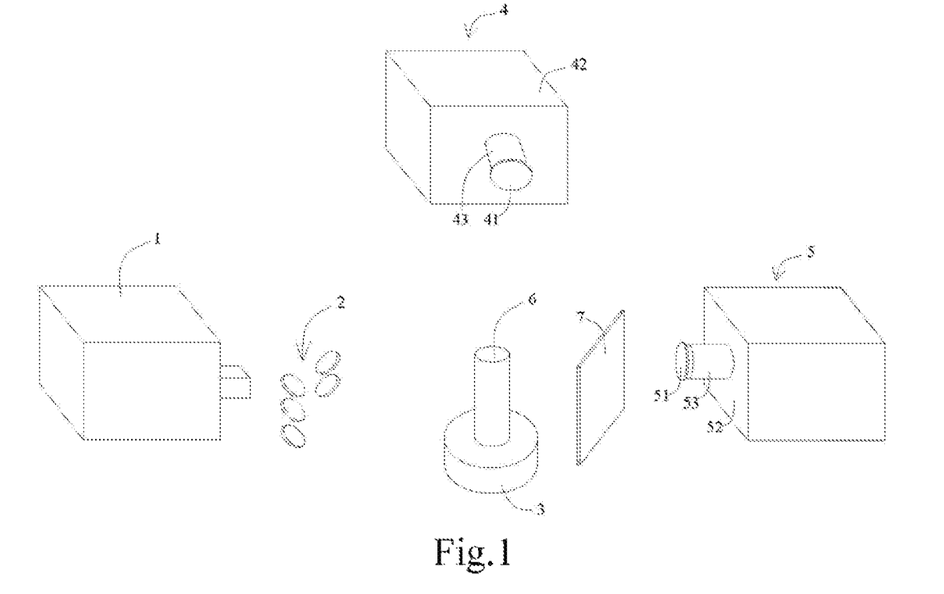
FIG. 1 is a schematic structural view of an apparatus for FMT of according to an exemplary embodiment of the disclosure.

Referring to FIG. 1, at least one embodiment of c apparatus for fluorescence molecular tomography (FMT) which is coupled with a computer product and may include an exciting light source, a carrying stage 3 and a receiving apparatus. The computer product includes a processor.

For example, the exciting light source may include a laser 1 and an exciting light adjusting mechanism 2, etc. The receiving apparatus may include a fluorescence detector 4, an exciting light detector 5 and a beam splitter 7, etc.

Wherein, the exciting light source may be used to provide an exciting light. Optionally, the exciting light source includes the laser 1 and the exciting light adjusting mechanism 2. For example, the laser 1 may include at least one from a solid laser, a gas laser, a semiconductor laser and a liquid laser, to which there is no particular limitation in the present disclosure.

The exciting light adjusting mechanism 2 may be used to split the exciting light into a plurality of exciting light beams. Optionally, the exciting light adjusting mechanism 2 may include a plurality of splitting mirrors 201 and a plurality of reflective mirrors 202 through which the exciting light is split into the plurality of exciting light beams.

Figure 2:
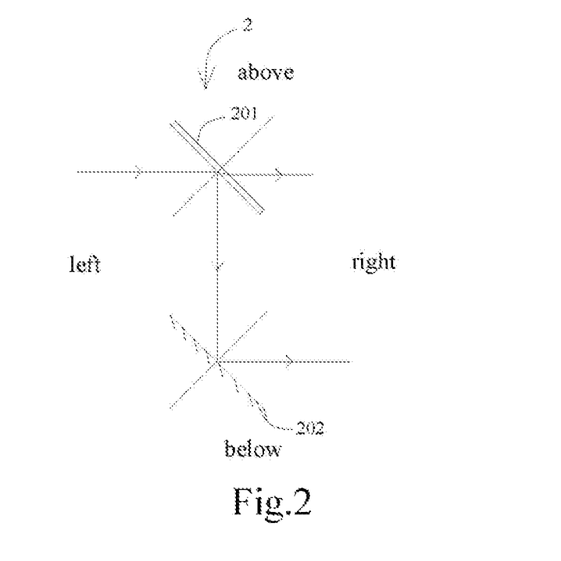
FIG. 2 is a schematic optical structural view of an exciting light adjusting mechanism as shown in FIG. 1 according to an exemplary embodiment.

In some embodiments, as shown in FIG. 2, the exciting light adjusting mechanism 2 may split the exciting light into two exciting light beams. The exciting light adjusting mechanism 2 may include a splitting mirror 201 and a reflective 202, etc. The splitting mirror 201 has an optical axis at a selected angle with respect to the exciting light, i.e., the splitting mirror 201 may be obliquely arranged relative to the exciting light, such that the exciting light is obliquely incident on the splitting mirror 201 which may split the exciting light into two exciting light beams by reflection and transmission, i.e., a reflected light beam and a transmitted light beam. The reflective mirror 202 may be arranged parallel to the splitting mirror 201 and used to reflect and allow one of the exciting light beams having passed through the splitting mirror 201 to be parallel to another exciting light beam. In the exemplary embodiment, the selected angle of the splitting mirror 201 with respect to the exciting light is about 45°. The reflective mirror 202 may be positioned below the splitting mirror 201. The reflective mirror 202 again reflects the reflected light and allows the again reflected light to be parallel to the transmitted light. Accordingly, two exciting light beams are formed and directed towards the subject to be examined.

Figure 3:
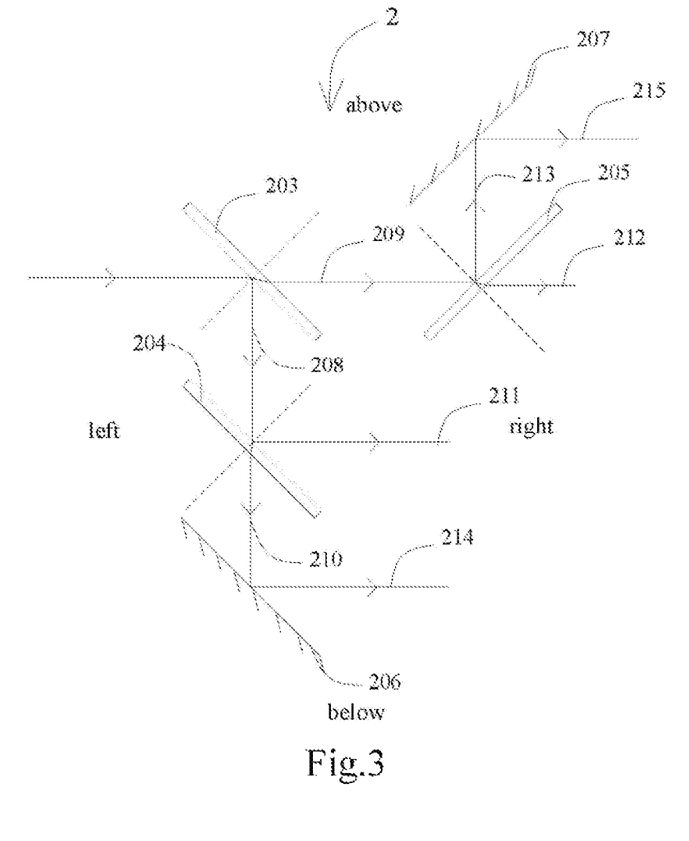
FIG. 3 is a schematic optical structural view of an exciting light adjusting mechanism in FIG. 1 according to another exemplary embodiment.

Optionally, the reflective mirror 202 may be positioned to the right of the splitting mirror 201. The reflective mirror 202 reflects the transmitted light and allows the reflected transmitted light to be parallel to the reflected light. Similarly, also two exciting light beams are formed and directed towards the subject to be examined. The angle of the splitting mirror 201 with respect to the exciting light may alternatively be set to be 20°, 30°, 40°, 41° and the like. In some embodiments, as shown in FIG. 3, the exciting light adjusting mechanism 2 may evenly split the exciting light into four exciting light beams. The exciting light adjusting mechanism 2 may include a first splitting mirror 203, a second splitting mirror 204, a first reflective mirror 206, a third splitting mirror 205 and a second reflective mirror 207, and so on. The optical axis of the first splitting mirror 203 is at a predetermined angle with respect to the exciting light, i.e., the first splitting mirror 203 is obliquely arranged relative to the exciting light. The first splitting mirror 203 serves to split the exciting light into two exciting light beams by reflection and transmission. The second splitting mirror 204 is arranged parallel to the first splitting mirror 203 and serves to split one of the exciting light beams having passed through the first exciting light beams 203 into two exciting light beams. The first reflective mirror 206 is arranged parallel to the first splitting mirror 203 and serves to reflect and allow one of the exciting light beams having passed through the second splitting mirror 204 to be parallel to another exciting light beam having passed through the second splitting mirror 204 and another exciting light beam having passed through the first splitting mirror 203. The third splitting mirror 205 is arranged perpendicular or parallel to the first splitting mirror 203 and serves to split the another exciting light beam having passed through the first splitting mirror 203 into two exciting light beams. The second reflective mirror 207 is arranged parallel to the third splitting mirror 205 and serves to reflect and allow one of the exciting light beams having passed through the third splitting mirror 205 to be parallel to another exciting light beam having passed through the third splitting mirror 205.

Alternative, the selected angle between the first splitting mirror 203 and the exciting light is about 45°. The second splitting mirror 204 is parallel to and positioned below the first splitting mirror 203. The first reflective mirror 206 is parallel to the first splitting mirror 203 and positioned below the second splitting mirror 204. The third splitting mirror 205 is perpendicular to and positioned to the right of the first splitting mirror 203. The second reflective mirror 207 is parallel to and positioned above the third splitting mirror 205. The first, second and third splitting mirror 203, 204 and 205 may be a neutral splitting mirror 201 with the ratio of transmission to reflection being 50/50. The first splitting mirror 203 evenly splits the exciting light into two exciting light beams by transmission and reflection, i.e., the first reflected light 208 and the first transmitted light 209. The second splitting mirror 204 evenly splits the first reflected light 208 into two exciting light beams, i.e., the second transmitted light 210 and the second reflected light 211 which is parallel to the first transmitted light 209. The third splitting mirror 205 evenly splits the first transmitted light 209 into two exciting light beams, i.e., the third transmitted light 212 and the third reflected light 213. The first reflective mirror 206 reflects the second transmitted light 210 to form the fourth reflected light 214 such that the fourth reflected light 214 is parallel to the second reflected light 211 and the first transmitted light 209. The second reflective mirror 207 reflects the third reflected light 213 to form the fifth reflected light 215 such that the fifth reflected light 215 is parallel to the second reflected light 211 and the first transmitted light 209. As such, the exciting light may be evenly split into four exciting light beams consisting of the fifth reflected light 215, the third transmitted light 212, the second reflected light 211 and the fourth reflected light 214. The four exciting light beams are directed towards the subject to be examined 6.

Optionally, the second splitting mirror 204 and the first reflective mirror 206 may be positioned to the right or left of the first splitting mirror 203, while the third splitting mirror 205 and the second reflective mirror 207 may be positioned above or below the first splitting mirror 203. As shown in FIG. 3, since the exciting light comes from the left, the exciting light adjusting mechanism 2 is correspondingly positioned at the right. At the position where the exciting light emits, the components and parts of different exciting light adjusting mechanisms 2 have different positions.

Optionally, the third splitting mirror 205 may be arranged parallel to the first splitting mirror 203. In such a case, the second reflective mirror 207 may be parallel to and positioned below the third splitting mirror 205. The angle of the splitting mirror 203 with respect to the exciting light may alternatively be set to be 20°, 30°, 40°, 41° and the like.

Figure 4:
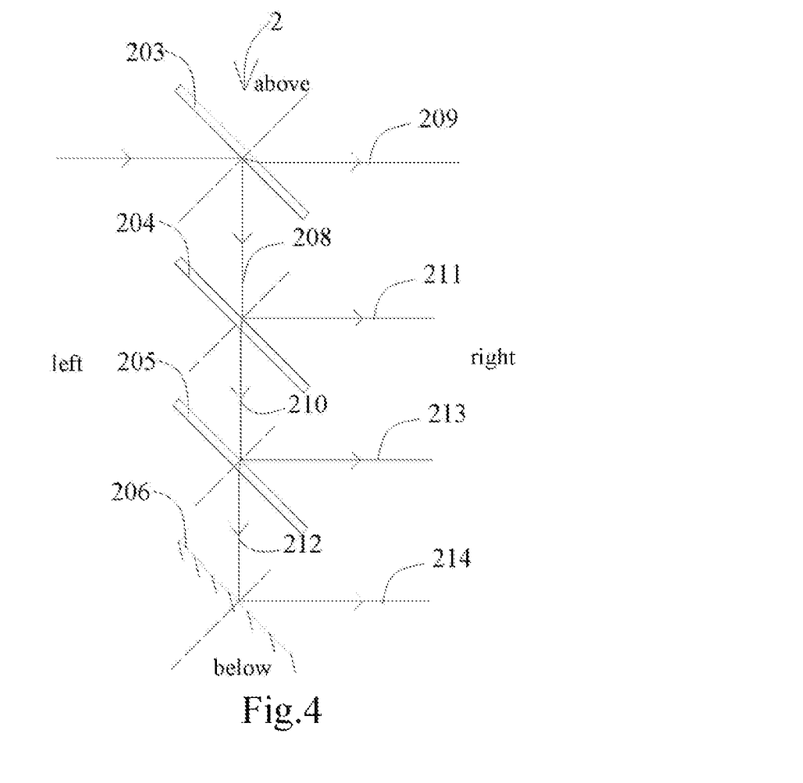
FIG. 4 is a schematic optical structural view of an exciting light adjusting mechanism in FIG. 1 according to still another exemplary embodiment.

In some embodiments, as shown in FIG. 4, the exciting light adjusting mechanism 2 may split the exciting light into four exciting light beams. The exciting light adjusting mechanism 2 may include a first splitting mirror 203, a second splitting mirror 204, a third splitting mirror 205, and a first reflective mirror 206, and so on. The optical axis of the first splitting mirror 203 is at a selected angle with respect to the exciting light, i.e., the first splitting mirror 203 is obliquely arranged relative to the exciting light. The first splitting mirror 203 serves to split the exciting light into two exciting light beams. The second splitting mirror 204 is arranged parallel to the first splitting mirror 203 and serves to split one of the exciting light beams having passed through the first exciting light beams 203 into two exciting light beams. The third splitting mirror 205 is arranged parallel to the second splitting mirror 204 and serves to split one of the exciting light beams having passed through the second exciting light beams 204 into two exciting light beams. The first reflective mirror 206 is arranged parallel to the third splitting mirror 205 and serves to reflect and allow one of the exciting light beams having passed through the third splitting mirror 205 to be parallel to another exciting light beam. The first, second and third splitting mirrors 203, 204 and 205 and the first reflective mirror 206 are coaxially arranged in the direction either perpendicular or parallel to the exciting light to split the exciting light into four exciting light beams.

Optionally, the selected angle between the first splitting mirror 203 and the exciting light is about 45°. The second splitting mirror 204 is parallel to and positioned below the first splitting mirror 203. The third splitting mirror 205 is parallel to and positioned below the second splitting mirror 204. The first reflective mirror 206 is parallel to the first splitting mirror 203 and positioned below the third splitting mirror 205. The first splitting mirror 203 splits the exciting light into two exciting light beams by transmission and reflection, i.e., the first reflected light 208 and the first transmitted light 209. The second splitting mirror 204 splits the first reflected light 208 into two exciting light beams, i.e., the second transmitted light 210 and the second reflected light 211 which is parallel to the first transmitted light 209. The third splitting mirror 205 splits the second transmitted light 210 into two exciting light beams, i.e., the third transmitted light 212 and the third reflected light 213 which is also parallel to the first transmitted light 209. The first reflective mirror 206 reflects the third transmitted light 212 to form the fourth reflected light 214 such that the fourth reflected light 214 is also parallel to the first transmitted light 209. As such, the exciting light may be evenly split into four exciting light beams consisting of the first transmitted light 209, the second reflected light 211, the third reflected light 213 and the fourth reflected light 214. The four exciting light beams are directed towards the subject to be examined 6. The ratio of transmission to reflection for the first, second and third splitting mirror 203, 204 and 205 may be determined on demand. For example, in the solution, the ratio of transmission to reflection for the first splitting mirror 203 is 1:3, the ratio of transmission to reflection for the second splitting mirror 204 is 2:1, and the ratio of transmission to reflection for the third splitting mirror 205 is 1:1. Such an arrangement allows the first transmitted light 209, the second reflected light 211, the third reflected light 213 and the fourth reflected light 214 to have relatively even intensity.

Optionally, the second splitting mirror 204, the third splitting mirror 205 and the first reflective mirror 206 may be positioned sequentially in parallel to the right or left of the first splitting mirror 203. As shown in FIG. 4, since the exciting light comes from the left in FIG. 3, the exciting light adjusting mechanism 2 is correspondingly positioned at the right. At the position where the exciting light emits, the components and parts of different exciting light adjusting mechanisms 2 have different positions. In addition, the angle of the splitting mirror 201 with respect to the exciting light may be set to be 20°, 30°, 40°, 41° and the like.

The exciting light adjusting mechanism splits the exciting light into a plurality of exciting light beams which illuminate simultaneously a plurality of sites of the subject to be examined such that the fluorescent substance at many sites are excited, thereby implementing an efficient excitement of the fluorescent substance, avoiding use of multiple-round collection of fluorescence in the relevant art, being capable of reducing efficiently experimental time, decreasing change in position of the subject to be examined due to discomfort of the subject to be examined caused by overlong experimental time, improving accuracy of the experimental results, raising the imaging speed, alleviating the photobleaching occurred with the prolongation of the experimental time, and improving accuracy of the experimental results.

In some embodiments, the exciting light source, the receiving apparatus and the subject to be examined are rotatable relatively to each other such that the processor can generate the 3D fluorescence distribution image.

It will be easily understood that any technical solution for relative rotation commonly used in the mechanical field may be applied in the technical solution of the disclosure. In some embodiments, the exciting light source and the receiving apparatus are fixedly positioned while the carrying stage is rotatable to rotate the subject to be examined. In some embodiments, the carrying stage is fixedly positioned while the exciting light source and the receiving apparatus are rotatable about the carrying stage as center. The carrying stage 3 may serve to carry the subject to be examined 6 and can rotate so as to drive the subject to be examined 6 to rotate. The subject to be examined 6 receives the plurality of exciting light beams to excite fluorescence. The carrying stage, for example, may be an electric rotating stage. The electric rotating stage can be continuously rotated by 360°, can be controlled to stop at any time, has a high revolution precision, and improve the accuracy of the experimental results.

The beam splitter serves to allow the fluorescence to exit in a first direction and the exciting light having passed through the subject to be examined to exist in a second direction. The first direction may a reflection direction while the second direction may be a transmission direction. On the contrary, the first direction may be the transmission direction while the second direction may be the reflection direction.

Alternative, the beam splitter 7 may be positioned between the carrying stage 3 and the fluorescence detector 4, or between the carrying stage 3 and the exciting light detector 5. For example, the beam splitter 7 is positioned between the carrying stage 3 and the exciting light detector 5. The beam splitter 7 is used to reflect the fluorescence to the fluorescence detector 4, and transmit the exciting light having passed through the subject to be examined 6 to the exciting light detector 5.

In some embodiments, the beam splitter may be a thin film splitting mirror. In some embodiments, the beam splitter may be a dichroic splitting mirror.

For example, in the following, a description will be made for the dichroic splitting mirror, which is also called as a dichromatic mirror. The beam splitter 7 almost completely transmits a light of certain wavelength while almost completely reflects lights of some other wavelength. The beam splitter 7 is positioned between the carrying stage 3 and the exciting light detector 5, and almost completely reflects the fluorescence while almost completely transmits the exciting light. Of course, in other exemplary embodiments, a beam splitter 7 may alternatively be chosen which almost completely transmits the fluorescence while almost completely reflects the exciting light, and thus may be positioned between the carrying stage 3 and the fluorescence detector 4.

The fluorescence detector 4 may be configured to receive and transform the fluorescence into a first electric signal. For example, the fluorescence detector 4 may include an exciting light filter 41 for filtering out the exciting light and a first imaging device 42 for receiving and transforming the fluorescence into an electric signal, and so on. Filtering the exciting light out by the exciting light filter 41 can avoid not only damage of the first imaging device 42 by the exciting light, but also noises caused by the exciting light, thereby improving the accuracy of the experimental results.

In some embodiments, the fluorescence detector 4 may further include a first optical lens 43 for adjusting the fluorescence beam.

Optionally, the first imaging device 42 may be a charge-coupled device (CCD) imaging modular or complementary metal oxide semiconductor (COMS) imaging modular and the like. The exciting light detector 5 may be configured to receive and transform the exciting light having passed through the subject to be examined 6 into a second electric signal. For example, the exciting light detector 5 may include a fluorescence filter 51 for filtering out the fluorescence and a second imaging device 52 for receiving and transforming the exciting light having passed through the subject to be examined 6 into an electric signal, and so on. Filtering the fluorescence out by the fluorescence filter 51 can avoid noises caused by the fluorescence, thereby improving the accuracy of the experimental results.

In some embodiments, the exciting light detector 5 may further include a second optical lens 53 for adjusting the exciting light beam.

Optionally, the second imaging device 52 may be a CCD imaging modular or COMS imaging modular and the like.

Figure 6:
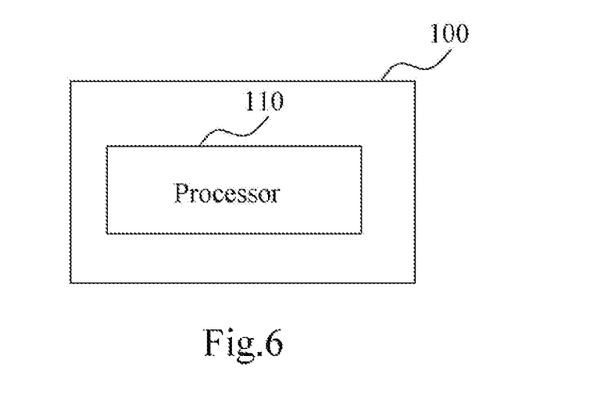
FIG. 6 is a schematic view of a computer product according to an exemplary embodiment of the disclosure.
Figure 7:
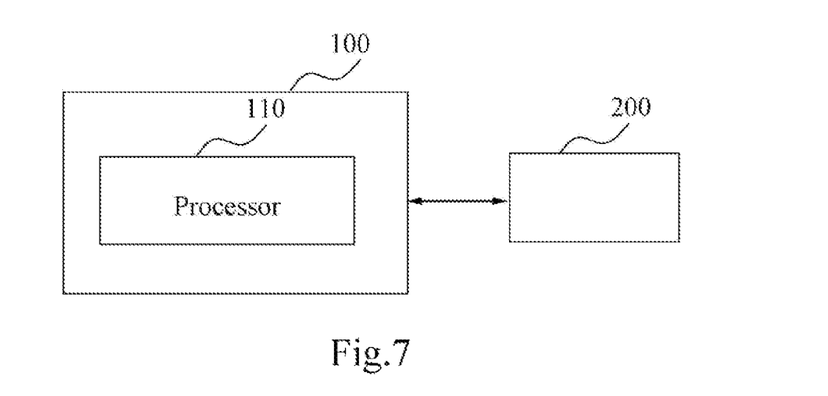
FIG. 7 is a schematic view which shows an apparatus for fluorescence molecular tomography is coupled with a computer product according to an exemplary embodiment of the disclosure.

An embodiment of the present disclosure provides a computer product. As shown in FIGS. 6 and 7, the apparatus for fluorescence molecular tomography 200 is coupled with the computer product 100. The computer product 100 includes a processor 110. The processor 100 is configured to reconstruct fluorescence based on the first and second electric signals.

For example, in the case where the exciting light source and the receiving apparatus and the subject to be examined are rotatable relatively to each other, the processor may be provided to generate a 3D fluorescence distribution image within the body of the subject to be examined 6 based on the first and second electric signals.

Optionally, the processor is a processing apparatus for executing logic operation, for example apparatus with capabilities of data processing and/or program executing, such as a central processing unit (CPU), a field programmable logic array (FPGA), a digital signal processor (DSP), a microcontroller (MCU), a dedicated logic circuit (ASIC), an image processor (GPU).

Optionally, the processor may be one or more processors.

It is easy to understand that the processor is usually coupled with a memory on which any combination of one or more computer program products is stored. The processor executes a computer instruction corresponding to a program to generate a 3D fluorescence distribution image. The memory may include various forms of computer-readable storage media, such as volatile memory and/or non-volatile memory. Volatile memory may include random access memory (RAM) and/or cache, for example.

Non-volatile memory may include, for example, read only memory (ROM), hard disk, erasable programmable read-only memory (EPROM), USB memory, flash memory, and the like. Various applications and various data may also be stored in a computer-readable storage medium, such as various data used and/or generated by the applications.

It can be easily understood that the processor is coupled with the apparatus which generates the first electrical signal and the second electrical signal (a fluorescent detector, a laser detector) to obtain the first electrical signal and the second electrical signal for fluorescence reconstruction.

For example, coupling includes connecting via a wireless network, a wired network, and/or any combination of a wireless network and a wired network. The network may include a local area network, the Internet, a telecommunications network, an internet of things and/or telecommunications network based internet of things, and/or any combination of the above networks. For example, the wired network may use metal wiring, twisted pair, coaxial cable, or optical fiber transmission for information transmission.

For example, the wireless network may use a communicating mode such as wireless wide area network (WWAN) mobile communication network, Bluetooth, Zigbee, or Wi-Fi.

For example, generating the 3D fluorescence distribution image within the body of the subject to be examined 6 based on the first and second electric signals includes: obtaining from $$\frac{y_f}{y_x} = A\mu_f(r)$$

a 3D absorption coefficient distribution of fluorescence within the body of the subject to be examined 6, where A is a projection matrix, $\mu_f(r)$ is 3D absorption coefficient distribution of fluorescence within the body of the subject to be examined 6, $y_x$ is the intensity of the exciting light having passed through the subject to be examined 6 and received by the exciting light detector 5, and $y_f$ is the intensity of the fluorescence received by the fluorescence detector 4.

Fluorescence molecular tomography apparatus and computer products can be of either split or integrated design. For example, a computer product is integrated with a fluorescent molecular tomography apparatus to form a fluorescent molecular tomography system. For example, a computer product is a server at a remote site or at a cloud end (relative to the fluorescent molecular tomography apparatus) that acquires one or more signals output from the fluorescence molecular tomography apparatus to generate a fluorescence distribution image.

Figure 5:
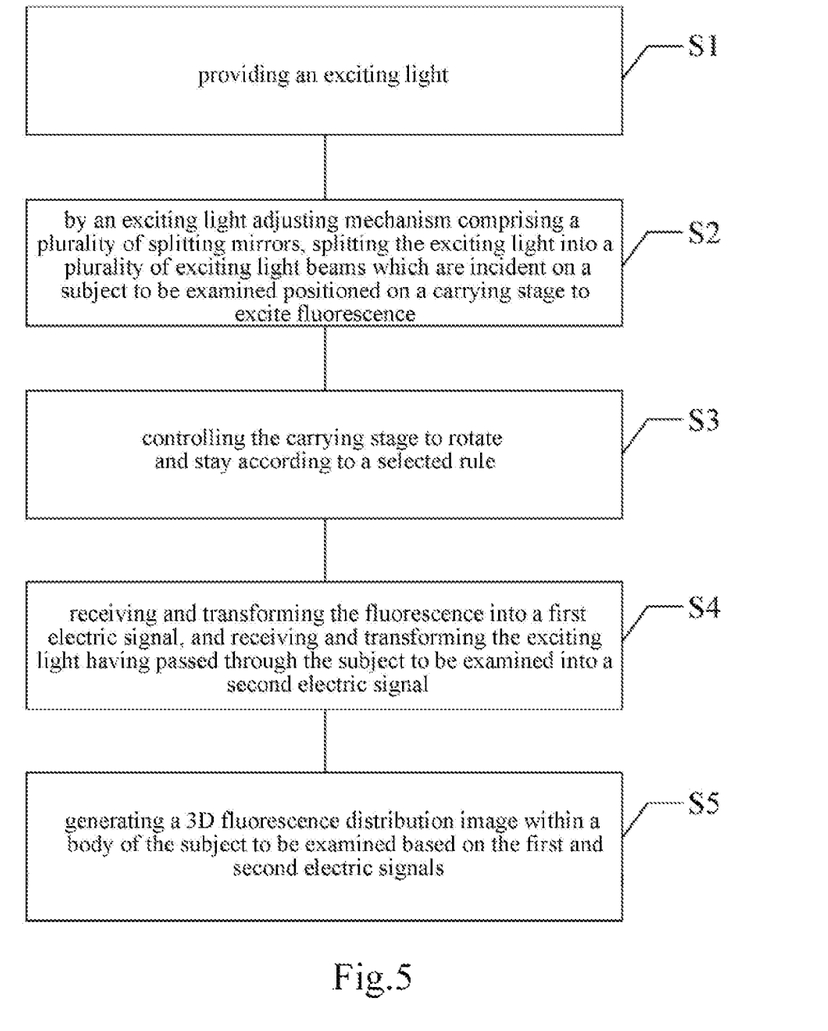
FIG. 5 is a schematic flow chart of a method for FMT according to an exemplary embodiment of the disclosure.

Referring to FIG. 5 which shows a schematic flow chart of a method for FMT according to an exemplary embodiment of the disclosure. The method for FMT may include: S1: providing an exciting light; S2: by the exciting light adjusting mechanism 2 comprising the plurality of splitting mirrors 201, splitting the exciting light into a plurality of exciting light beams which are incident on the subject to be examined 6 positioned on the carrying stage 3 to excite fluorescence; S3: controlling the carrying stage 3 to rotate and stay according to a selected rule; S4: receiving and transforming the fluorescence into a first electric signal, and receiving and transforming the exciting light having passed through the subject to be examined 6 into a second electric signal; and S5: generating the 3D fluorescence distribution image within the body of the subject to be examined 6 based on the first and second electric signals.

Hereinafter detailed description will be made for a working process of the method for FMT.

In some embodiments, the subject to be examined containing fluorescent substance is fixed on the rotating stage 3, and positioned at its center as much as possible. The laser is turned on and the exciting light impinges on the surface of the subject to be examined 6. The fluorescence detection apparatus 4 and the exciting light detection apparatus 5 are operated for trial photo capture in order to adjust the exposure parameters and pixel combination parameters of the first imaging device 42 of the fluorescence detection apparatus 4 and the second imaging device 52 of the exciting light detection apparatus 5, ensuring that the intensity of the fluorescence and the exciting light is within the optimum measurement ranges of the first and second imaging devices 42 and 52. A starting position is set where the laser is maintained to operate such that the exciting light is split into a plurality of exciting light beams by the exciting light adjusting mechanism 2 which impinge on the surface of the subject to be examined 6 and excite the fluorescent substance within the body of the subject to be examined 6 to generate fluorescence. The exciting light and the fluorescence are transmitted outside of the body of the subject to be examined 6 after being scattered and absorbed. The first and second imaging devices 42 and 52 are controlled to simultaneously collect the fluorescence and the exciting light, respectively. The rotating stage 3 performs a plurality of rotations by a selected angle from the starting position, with a stop for a selected period of time following each rotation, until the rotating stage 3 completes a revolution. During each stop for the selected period of time, the fluorescence detection apparatus 4 receives and transforms the fluorescence into a first electric signal and the exciting light detection apparatus 5 receives and transforms the exciting light having passed through the subject to be examined 6 into a second electric signal. The processor generates a 3D fluorescence distribution image with the body of the subject to be examined 6 based on the first and second electric signals.

Generating the 3D fluorescence distribution image within the body of the subject to be examined 6 based on the first and second electric signals includes: obtaining from $$\frac{y_f}{y_x} = A\mu_f(r)$$

a 3D absorption coefficient distribution of fluorescence within the body of the subject to be examined 6, where A is a projection matrix, $\mu_f(r)$ is 3D absorption coefficient distribution of fluorescence within the body of the subject to be examined 6, $y_x$ is the intensity of the exciting light having passed through the subject to be examined 6 and received by the exciting light detector 5, and $y_f$ is the intensity of the fluorescence received by the fluorescence detector 4.

For example, propagation of the fluorescence in the subject to be examined 6 is described by a pair of coupled diffusion equations:

$$\begin{cases} -\nabla \cdot [D(r)\nabla \phi_x(r', r)] + \mu(r)\phi_x(r', r) = \Theta(r) \\ -\nabla \cdot [D(r)\nabla \phi_f(r'', r)] + \mu(r)\phi_f(r'', r) = \eta\mu_f\phi_x(r') \end{cases} \quad (1)$$

Wherein, D(r) is the diffusion coefficient, r is a position within the body of the subject to be examined 6, r' is the position of the exciting light source at the surface of the subject to be examined 6 to which r corresponds, r" is the position of the fluorescence at the surface of the subject to be examined 6 to which r corresponds, $\phi_x(r',r)$ is the photon density of the exciting light at the position of r', $\phi_f(r'',r)$ is the photon density of the fluorescence at the position of r", $\mu(r)$ is the absorption coefficient at r, $\Theta(r)$ is the term for the exciting light source, $\eta$ is the fluorescence quantum productivity, and $\mu_f$ is the absorption coefficient of the fluorescent substance absorbing the exciting light.

When the light source is an illuminating light beam, the term for light source becomes $\Theta(r)=\delta(r-r_s)$, where $r_s$ is the position of the incident light. In such a case, the intensity of exciting light $\phi_x(r',r)$ at the position of r within the body of the subject to be examined 6 is the Green function solution $G(r_s,r)$ for the diffusion equations (1). When the light source turns to a plurality of illuminating light beams from one illuminating light beam, the term for light source becomes $$\Theta(r) = \sum_{i=1}^{n} \delta(r - r'_i)$$

Wherein, $r_i'$ is the position of the ith light source at the surface of the subject to be examined 6, n is the number of the incident light sources, in such as case, the intensity of exciting light $\phi_x(r',r)$ at the position of r within the body of the subject to be examined 6 is the sum of the intensities of exciting lights from a plurality of light sources:

$$\phi_x(r', r) = \sum_{i=1}^{n} G(r'_i, r) \quad (2)$$

Wherein, $G(r_i', r)$ is the Green function solution for the diffusion equations (1) when the light sources are $r_i'$ and r.

Now the intensity of exciting light $\phi_x(r', r_d)$ and the intensity of fluorescence $\phi_f(r', r_d)$ at the position of $r_d$ at the body surface of the subject to be examined 6 are $$\phi_x(r', r_d) = \sum_{i=1}^n G(r_i', r_d) \quad (3)$$

$$\phi_f(r', r_d) = \int \eta \mu_f \phi_x(r', r) G(r, r_d) dr \quad (4)$$

The intensity of the fluorescence impinging on the first imaging device 42 from the body surface of the subject to be examined 6 is $y_f$, the intensity of the exciting light impinging on the second imaging device 52 from the body surface of the subject to be examined 6 is $y_x$, and the impinging transform factor is P, then $$y_f = P \cdot \phi_f(r', r_d) \quad (5)$$

$$y_x = P \cdot \phi_x(r', r_d) \quad (6)$$

In order to remove the impinging transform factor, the formula (5) is divided by the formula (6) and then $$\frac{y_f}{y_x} = \frac{\phi_f(r', r_d)}{\phi_x(r', r_d)} = \frac{1}{\phi_x(r', r_d)} \int \eta \mu_f(r) \phi_x(r', r) G(r, r_d) dr = A \mu_f(r) \quad (7)$$

Wherein, A is the projection matrix, $\mu_f(r)$ is the 3D absorption coefficient distribution of fluorescence within the body of the subject to be examined 6, $y_x$ is the intensity of the exciting light having passed through the subject to be examined 6 and received by the exciting light detector 5, and $y_f$ is the intensity of the fluorescence received by the fluorescence detector 4.

Enter $y_f$ and $y_x$ to the equation (7) for solution then obtain the 3D absorption coefficient distribution of fluorescence $\mu_f(r)$.

It can be known from the technical solutions of the above embodiments that the disclosure at least has at least one of the following advantages and positive effects.

With the apparatus for FMT and the method for FMT of the disclosure, the fluorescence and the exciting light are split by the beam splitter, and then directed towards the fluorescence detector and the exciting light detector, respectively, by which the exciting light and the fluorescent from the same site can be collected simultaneously, thereby avoiding use of the method in the relevant art of collecting a round of exciting light images followed by collecting a round of fluorescence images. With the apparatus and the method, the experimental time can be reduced efficiently, change in position of the subject to be examined due to discomfort of the subject to be examined caused by overlong experimental time can be decreased, the imaging speed is raised, the photobleaching occurred with the prolongation of the experimental time is alleviated, and the accuracy of the experimental results is improved.

The aforesaid features, structures and characteristics may be combined into one or more embodiments in any appropriate way, and the features discussed with reference to the respective embodiments are exchangeable if feasible. In the above description many details are provided for full understanding of the embodiments of the disclosure. However, those skilled in the art will realize that the technical solutions of the disclosure may be practiced without one or more of the particular details, and may use other methods, components, materials, etc. In some cases, the known structures, materials or operations are not shown or described in detail in order not to obscure the aspects of the disclosure.

The usage of "approximate", "about" and the like in the specification typically means to be within 20% of a given value or range, preferably within 10%, and more preferably within 5%. The numbers given herein mean approximate numbers, i.e., implicitly contain the meaning of "approximate", "about", "or so", or "roughly" unless otherwise stated.

Although in the specification, relative words such as "above" or "below" are used to describe a relative relationship of one component with another one, they are used herein only for convenience, for example, based on the exemplary directions as shown in the figures. It would be understood that if the apparatus shown in the figures are reversed such that they are turned upside down, the components described as being "above" will become those being "below". Other relative words such as "left" and "right" also have the similar meanings. When a structure is "on" another structure, it is possible that the structure is integrally formed on the another structure, or the structure is "directly" disposed on the another structure, or the structure is "indirectly" disposed on the another structure by means of still another structure.

In the specification the words such as "a", "an", "the", "said" and "at least one" are used to indicate that there is one or more elements/component parts/and the like. The words such as "comprise", "include", "have" and "has" are used to indicate an opening meaning of including something therein and that there may be other elements/component parts/and the like in addition to the listed elements/component parts/ and the like. The words such as "first", "second" and "third" are only used for indication and not intended to limit the number of the subject.

It should be appreciated that the disclosure is not intended to limit its usage to the detailed structures and arrangements as set forth in the specification. The disclosure, however, may have other embodiments and be achieved and carried out by various ways. The aforesaid variants and modified versions fall within the scope of the disclosure. It should be appreciated that the disclosure as disclosed and defined in the specification extends to all of alternative combinations of two or more separate features mentioned in or obvious from the specification and/or figures. All those different combinations constitute a plurality of alternative aspects of the disclosure. The embodiments as described in the specification show the known best modes for the disclosure and enable those skilled in the art to use the disclosure.

What is claimed is:

1. An apparatus for fluorescence molecular tomography coupled with a computer product, and the apparatus comprising:

an exciting light source configured to provide an exciting light;

a carrying stage configured to carry a subject to be examined which receives the exciting light to excite fluorescence;

a receiving apparatus comprising a fluorescence detector, an exciting light detector and a beam splitter, wherein the beam splitter is configured to allow the fluorescence to exit in a first direction and the exciting light having passed through the subject to be examined to exit in a second direction;

the fluorescence detector is positioned in the first direction to the beam splitter and configured to receive and detect the intensity of the fluorescence; and the exciting light detector is positioned in the second direction to the beam splitter and is configured to receive and detect the intensity of the exciting light having passed through the subject to be examined; and the computer product comprises a processor configured to reconstruct a fluorescence distribution image based on the first and second electrical signals, wherein the reconstruction of the fluorescence distribution image comprises generation of a 3D fluorescence distribution image;

wherein the processor is configured to generate 3D fluorescence distribution image within the subject to be examined based on the first and second electric signals, which comprises;

a 3D absorption coefficient distribution of fluorescence within the subject to be examined is obtained from $$\frac{y_f}{y_x} = \frac{\phi_f(r', r_d)}{\phi_X(r', r_d)} = \frac{1}{\phi_x(r', r_d)} \int \eta \mu_f(r) \phi_x(r', r) G(r, r_d) dr = A\mu_f(r),$$

where A is a projection matrix $\mu_f(r)$ is 3D absorption coefficient distribution of fluorescence within the subject to be examined, $y_x$ is intensity of the exciting light having passed through the subject to be examined and received by the exciting light detector, $y_f$ is intensify of the fluorescence received by the fluorescence detector, $\phi_x(r', r_d)$ is the intensity of the exciting light at the position of $r_d$ at the body surface of the subject to be examined $\phi_f(r', r_d)$ is the intensity of the fluorescence at the position of $r_d$ at the body surface of the subject to be examined, $\eta$ is a fluorescence quantum productivity, $\phi_x(r'r_d)$ is a photon density of the exciting light at a position of r', and $G(r, r_d)$ is a Green function solution of the exciting light at the position of $r_d$ and r.

2. The apparatus for fluorescence molecular tomography according to claim 1, wherein the exciting light source and the receiving apparatus are rotatable relatively to the subject to be examined to enable the processor to generate a 3D fluorescence distribution image.

3. The apparatus for fluorescence molecular tomography according to claim 1, wherein the exciting light source and the receiving apparatus are fixedly positioned, while the carrying stage is rotatable to rotate the subject to be examined.

4. The apparatus for fluorescence molecular tomography according to claim 1, wherein the carrying stage is fixedly positioned, while the exciting light source and the receiving apparatus are rotatable about the carrying stage as a center.

5. The apparatus for fluorescence molecular tomography according to claim 1, wherein the fluorescence detector comprises:

an exciting light filer configured to filter out the exciting light; and a first imaging device configured to receive and to transform the fluorescence into a first electric signal.

6. A method for fluorescence molecular tomography, being applied in the apparatus for fluorescence molecular tomography according to claim 1, wherein the method for fluorescence molecular tomography comprises:

providing an exciting light;

controlling the carrying stage, or controlling the exciting light source and the receiving apparatus, to rotate and stay according to a selected rule;

receiving and transforming the fluorescence into a first electrical signal, and at the same time receiving and transforming the exciting light having passed through the subject to be examined into a second electric signal; and generating a fluorescence distribution image within a body of the subject to be examined based on the first and second electrical signals;

wherein the step of generating the fluorescence distribution image within the body of the subject to be examined based on the first and second electric signals comprises generating a 3D fluorescence distribution image within the subject to be examined based on the first and second electric signals;

wherein the step of generating the 3D fluorescence distribution image within the body of the subject to be examined based on the first and second electric signals comprises;

a 3D absorption coefficient distribution of fluorescence within the body of the subject to be examined is obtained from $$\frac{y_f}{y_x} = \frac{\phi_f(r', r_d)}{\phi_X(r', r_d)} = \frac{1}{\phi_x(r', r_d)} \int \eta \mu_f(r) \phi_x(r', r) G(r, r_d) dr = A\mu_f(r),$$

where A is a projection matrix, $\mu_f(r)$ is 3D absorption coefficient distribution of fluorescence within the body of the subject to be examined, $y_x$ is intensity of the exciting light having passed through the subject to be examined and received by the exciting light detector, $y_f$ is intensify of the fluorescence received by the fluorescence detector, $\phi_x(r', r_d)$ is the intensity of the exciting light at the position of $r_d$ at the body surface of the subject to be examined, $\phi_f(r', r_d)$ is the intensity of the fluorescence at the position of $r_d$ at the body surface of the subject to be examined, $\eta$ is a fluorescence quantum productivity, $\phi_x(r',r)$ is a photon density of the exciting light at a position of r', and $G(r, r_d)$ is a Green function solution of the exciting light at the positions of $r_d$ and r.

* * * * *